US012111273B2

(12) United States Patent
Mitchell et al.

(10) Patent No.: US 12,111,273 B2
(45) Date of Patent: Oct. 8, 2024

(54) SYSTEMS AND METHODS FOR DETERMINING THE MINERALOGY OF DRILL SOLIDS

(71) Applicant: Schlumberger Technology Corporation, Sugar Land, TX (US)

(72) Inventors: Jonathan Mitchell, Cambridge (GB); Débora Campos de Faria, Cambridge (GB); Ashley Bernard Johnson, Cambridge (GB); Adam Colbourne, Cambridge (GB); Trevor Hughes, Cambridge (GB); Sean Lovett, Cambridge (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 110 days.

(21) Appl. No.: 18/063,729

(22) Filed: Dec. 9, 2022

(65) Prior Publication Data
US 2023/0184705 A1    Jun. 15, 2023

Related U.S. Application Data

(60) Provisional application No. 63/265,228, filed on Dec. 10, 2021.

(30) Foreign Application Priority Data

Dec. 30, 2021    (ID) .............................. P00202112335

(51) Int. Cl.
*G01N 24/08*    (2006.01)
*E21B 49/00*    (2006.01)
(Continued)

(52) U.S. Cl.
CPC ......... *G01N 24/081* (2013.01); *E21B 49/005* (2013.01); *G01N 21/65* (2013.01);
(Continued)

(58) Field of Classification Search
CPC .... G01N 24/081; G01N 21/65; G01N 23/223; G01N 33/2823; G01N 33/2835;
(Continued)

(56) References Cited

U.S. PATENT DOCUMENTS 4,699,002 A    10/1987    Rockley
5,532,593 A    7/1996    Maneval et al.
(Continued)

FOREIGN PATENT DOCUMENTS

FR    2810736 A1    12/2001
WO    2016071818 A1    5/2016

OTHER PUBLICATIONS

Akpa, B. S. et al., "In situ 13C DEPT-MRI as a tool to spatially resolve chemical conversion and selectivity of a heterogeneous catalytic reaction occurring in a fixed-bed reactor", Chemical Communications, 2005, 21, pp. 2741-2743.
(Continued)

*Primary Examiner* — G. M. A Hyder
(74) *Attorney, Agent, or Firm* — Jeffrey D. Frantz

(57) ABSTRACT

A method for measuring at least one property of a sample includes obtaining a sample of fluid including at least fines from a downhole environment, exposing the sample to a magnetic field, measuring a magnetic susceptibility of the fines in the sample in response to the magnetic field, and identifying at least one mineral present in the fines based at least partially on the magnetic susceptibility.

18 Claims, 11 Drawing Sheets

(51) Int. Cl.
G01N 21/65 (2006.01)
G01N 23/223 (2006.01)
G01N 33/28 (2006.01)
(52) U.S. Cl.
CPC ....... *G01N 23/223* (2013.01); *G01N 33/2823* (2013.01); *G01N 33/2835* (2013.01); *G01N 2223/076* (2013.01); *G01N 2223/507* (2013.01); *G01N 2223/637* (2013.01)
(58) Field of Classification Search
CPC ....... G01N 2223/076; G01N 2223/507; G01N 2223/637; G01N 21/3563; G01N 21/3581; E21B 49/005
See application file for complete search history.

(56) References Cited

U.S. PATENT DOCUMENTS

| | | | |
|---|---|---|---|
| 6,016,872 | A | 1/2000 | Davis |
| 6,290,001 | B1 | 9/2001 | West et al. |
| 8,627,902 | B2 | 1/2014 | Hammer et al. |
| 8,633,689 | B2 | 1/2014 | Li et al. |
| 8,710,836 | B2 | 4/2014 | Adolphi et al. |
| 8,781,762 | B2 | 7/2014 | MacLeod et al. |
| 9,121,550 | B2 | 9/2015 | Ong et al. |
| 9,244,026 | B2 | 1/2016 | Stock et al. |
| 9,329,122 | B2 | 5/2016 | Herron et al. |
| 10,697,910 | B2 | 6/2020 | Mitchell et al. |
| 10,989,646 | B1 * | 4/2021 | Jamison ............... E21B 49/005 |
| 11,268,371 | B2 | 3/2022 | Hammond |
| 2014/0361466 | A1 | 12/2014 | Kimour et al. |
| 2015/0122016 | A1 | 5/2015 | Tozzi et al. |
| 2015/0377998 | A1 | 12/2015 | Bendel |
| 2016/0108687 | A1 | 4/2016 | Rapoport |

OTHER PUBLICATIONS

Ali, A. et al. "Magnetic Susceptibility of Drill Cuttings in a North Sea Oil Well: A Rapid, Non-Destructive Means of Characterizing Lithology", Paper 036, presented at the International Symposium of the Society of Core Analysts held in St. John's Newfoundland and Labrador, Canada, 2015, 6 pages.

Allen, D. F. et al., "The Practical Application of NMR Logging in Carbonates: 3 Case Studies", SPWLA-2001-K paper presented at the SPWLA 42nd Annual Logging Symposium held in Houston, Texas, USA, 2001, 14 pages.

Arola, D. F. et al., "Use of nuclear magnetic resonance imaging as a viscometer for process monitoring", Chemical Engineering Science, 1997, 52(13), pp. 2049-2057.

Beck, F. E. et al., "The Effect of Rheology on Rate of Penetration", SPE/IADC 29368, presented at the SPE/IADC Drilling Conference, Amsterdam, Netherlands, 1995, 9 pages.

Blythe, T. W. et al., "Characterising the rheology of non-Newtonian fluids using PFG-NM Rand cumulant analysis", Journal of Magnetic Resonance, 2015, 255, pp. 122-131.

Brown, R. W. et al., "MR Angiography and Flow Quantification", Chapter 24 in Magnetic Resonance Imaging—Physical Principles and Sequence Design, John Wiley & Sons, New York, 2014, pp. 701-737.

Callaghan, P. T., "The Measurement of Motion Using Spin Echoes, Chapter 6 in Principles of Nuclear Magnetic Resonance microscopy", Oxford University Press, Oxford, 1991, pp. 328-370.

Caprihan, A. et al, "Flow Measurement by NMR", Physics Reports, 1990, 198(4), pp. 195-235.

Carr, H. Y. et al, "Effects of Diffusion on Free Precession in Nuclear Magnetic Resonance Experiments", Physical Review, 94, 1954, pp. 630-638.

Chen, Q. et al., "The internal magnetic field distribution, and single exponential magnetic resonance free induction decay, in rocks", Journal of Magnetic Resonance, 2005, 175, pp. 300-308.

Clark, P. E., "Drilling Mud Rheology and the API recommended measurements", SPE 29543, presented at the SPE Production Operations Symposium, Oklahoma City, Oklahoma, U.S.A., 1995, pp. 933-941.

Coskun, S. B. et al., "Estimation of permeability from image analysis of reservoir sandstones", Journal of Petroleum Science and Engineering, 1993, 10, pp. 1-16.

Cotts, R. M. et al., "Pulsed Field Gradient Stimulated Echo Methods for Improved NMR Diffusion Measurements in Heterogeneous Systems", Journal of Magnetic Resonance, 1989, 83(2), pp. 252-266.

Edwards, C. M. et al., "The Measurement of Fluid Velocities in Porous Media", SCA Conference Paper No. 9310, 1993, 15 pages.

Egermann, P. et al., "A Fast and Direct Method of Permeability Measurements on Drill Cuttings", SPE 77563, presented at the SPE Annual Technical Conference and Exhibition held in San Antonio, Texas, USA, SPE Reservoir Evaluation & Engineering, 2002, 8(4), 8 pages.

Emid, S. et al., "High Resolution NMR Imaging in Solids", Physica, 1985, 128(1), pp. 81-83.

Fens, T. W. et al., "Archie's Dream: Petrophysics From Sidewall Samples and Cuttings", SCA-9805, SCA Conference, 1998, 10 pages.

Fordham, E. J. et al., "Viscoplastic Flow in Centered Annuli, Pipes, and Slots", Industrial & Engineering Chemistry Research, 1991, 30, pp. 517-524.

Gibbs, S. J. et al., "NMR flow imaging of aqueous polysaccharide solutions", Journal of Rheology, 1994, 38, pp. 1757-1767.

Gibbs, S. J., "Strategies for Rapid NMR Rheometry by Magnetic Resonance Imaging Velocimetry", Journal of Magnetic Resonance, 1997, 125(1), pp. 43-51.

Gladden L. F. et al., "MRI: Operando measurements of temperature, hydrodynamics and local reaction rate in a heterogeneous catalytic reactor", Catalysis Today, 2010, 155, pp. 157-163.

Haacke, E. M. et al., "Magnetic Resonance Imaging ~ Physical Principles and Sequence Design", John Wiley & Sons, Inc., New York, 1999, Chapter 10, Section 10.4 "3D vol. Imaging", pp. 194-196.

Hahn, E. L. ,"Nuclear Induction Due to Free Larmor Precession", Physical Review, 1950, 77, pp. 297-298.

Han, M. et al., "Particle migration in tube flow of suspensions", Journal of Rheology, 199, 43, pp. 1157-1174.

Houwen, O. H. et al, "Rheology of Oil-Base Muds", SPE-15416-MS, presented at the SPE Annual Technical Conference and Exhibition, New Orleans, Louisiana, U.S.A., 1986, 12 pages.

Houwen, O. H. et al., "Measurement of Composition of Drilling Mud by X-ray Fluorescence", SPE/IADC 25704, presented at the 1993 SPE/IADC Drilling Conference, Amsterdam, Netherlands, pp. 277-286.

Hurlimann, M. D. et al., "The diffusion-spin relaxation time distribution function as an experimental probe to characterize fluid mixtures in porous media", Journal of Chemical Physics, 2002, 117(22), pp. 10223-10232.

Hussain, R. et al., "Monitoring water transport in sandstone using flow propagators: A quantitative comparison of nuclear magnetic resonance measurement with lattice Boltzmann and pore network simulations", Advances in Water Research, 2013, 60, pp. 64-74.

Johns, M. L., "NMR studies of emulsions", Current Opinion in Colloid & Interface Science, 2009, 14(3), pp. 178-183.

Johns, M. L. et al., Figure 1 in "Using MR Techniques to Probe Permeability Reduction in Rock Cores" AIChE Journal, 2003, 49(5), pp. 1076-1084.

Jullien, P. et al., "On the validation of magnetic resonance velocimetry in single-phase turbulent pipe flows", Journal of Magnetic Resonance, 2012, 216, pp. 101-106.

Kamath, J., "Evaluation of Accuracy of Estimating Air Permeability From Mercury Injection Data", SPE Formation Evaluation, 1992, 7(4), pp. 304-310, 1992.

Karger, J. et al., "The Propagator Representation of Molecular Transport in Microporous Crystallites", Journal of Magnetic Resonance, 1983, 51(1), pp. 1-7.

Katz, A. J. et al., "Quantitative prediction of permeability in porous rock", Physical Review B, 1986, 34(11), pp. 8179-8181.

(56) References Cited

OTHER PUBLICATIONS

Larson, R. G. et al., "Effects of Sample Size on Capillary Pressures in Porous Media", Powder Technology, 1981, 30 (2), pp. 123-138.

Lavenson, D. M. et al., "Yield Stress of Pretreated Corn Stover Suspensions Using Magnetic Resonance Imaging", Biotechnology Bioengineering, 2011, 108(10), pp. 2312-2319.

Leu, G. et al., "Fixed and pulsed gradient diffusion methods in low-field core analysis", Magnetic Resonance Imaging, 2005, 23(2), pp. 305-309.

Loannidis, M. A. et al., "Statistical analysis of the porous microstructure as a method for estimating reservoir permeability", Journal of Petroleum Science and Engineering, 1996, 16, pp. 251-261.

Loermans, T. et al., "Advance Mud Logging (AML) Aids Formation Evaluation and Drilling, and Yields Precise Hydrocarbon Fluid Composition", SPE141277, presented at the SPE Middle East Oil and Gas Show and Conference held in Manama, Bahrain, 2011, 12 pages.

Luffel, D. L., "Devonian shale matrix permeability successfully measured on cores and drill cuttings", Gas Shales Technology Review, 1993, 8(2), pp. 46-55.

Maglione, R. et al., "In-Situ Rheological Characterization of Drilling Mud", SPE-66285-PA, Spe Journal, 2000, 5(4), pp. 377-386.

Mansfield, P. et al.,"Fluid Transport in Porous Rocks. I. EPI Studies and a Stochastic Model of Flow", Journal of Magnetic Resonance, Series A, 1996, 122(2), pp. 137-148.

Marsala, A. F. et al. "Portable Energy-Dispersive X-Ray Fluorescence Integrates Mineralogy and Chemostratigraphy Into Real-Time Formation Evaluation", Petrophysics, 2012, 53(2), pp. 102-109.

McCarthy, K. L., et al., "Flow Profiles in a Tube Rheometer Using Magnetic Resonance Imaging", Journal of Food Engineering, 1992, 16, pp. 109-125.

Meiboom, S. et al., "Modified Spin-Echo Method for Measuring Nuclear Relaxation Times", Review of Scientific Instruments 29, 1958, pp. 688-691.

Merrill, M. R. et al.,"Velocity Measurements in Natural Porous Rocks", Magnetic Resonance Imaging, 1994, 12(2), pp. 345-348.

Merrill, M. R., "Local Velocity and Porosity Measurements Inside Casper Sandstone Using MRI", AIChE Journal, 1994, 40, pp. 1262-1267.

Miao, X. et al. "Discriminating the Mineralogical Composition in Drill Cuttings Based on Absorption Spectra in the Terahertz Range", Applied Spectroscopy, 2017, 71(2), pp. 186-193.

Mirotchnik, K. et al., "A Novel Method to Determine NMR Petrophysical Parameters From Drill Cuttings", Paper presented at the SPWLA 45th Annual Logging Symposium held in Noordwijk, The Netherlands, Jun. 6-9, 2004, 15 pages.

Mitchell, J. et al., "Contributed review: nuclear magnetic resonance core analysis at 0.3 T", Review of Scientific Instruments, 2014, 85(11), 111502, 17 pages.

Mitchell, J. et al., "Low-field permanent magnets for industrial process and quality control", Progress in Nuclear Magnetic Resonance Spectroscopy, 2014, 76, pp. 1-50; Section 3.1 "Permanent magnet configurations", pp. 6-8.

Mitchell, J. et al., "Magnetic resonance imaging in laboratory petrophysical core analysis", Physics Reports, 2013, 526, pp. 165-225; Section 4: "High resolution MRI in core analysis", pp. 183-198.

Mitchell, J. et al., "Nuclear magnetic resonance relaxation and diffusion in the presence of internal gradients : The effect of magnetic field strength", Physical Review E, 2010, 81, 206101, 19 pages.

Mitchell, J. et al., "Rapid Measurements of Diffusion Using PFG: Developments and Applications of the Difftrain Pulse Sequence", Concepts in Magnetic Resonance, 2009, 34A(1), pp. 1-15.

Mitchell, J. et al., "Real-time oil-saturation monitoring in rock cores with low-field NMR", Journal of Magnetic Resonance, 2015, 256, pp. 34-42.

Mitchell, J., "Can sodium NMR provide more than a tracer for brine in petrophysics", Journal of Petroleum Science and Engineering, 2016, 146, pp. 360-368.

Nes, O. M. et al., "Rig Site and Laboratory Use of CWT Acoustic Velocity Measurements on Cuttings", SPE 50982, SPE Reservoir Evaluation Engineering, 1998, 1(4), 6 pages.

Nigh, E. et al., "P-K: Wellsite Determination of Porosity and Permeability Using Drilled Cuttings", Paper presented at the C.W.L. Society 10th Formation Evaluation Symposium, CWLS Journal, 1984, 13(1), 16 pages.

Nikitin, A. et al. "Automated Mud Logging System as a Cost-Efficient Way of Acquiring Subsurface Data: Results of the Field Trial", SPE-187387-MS, 2017, presented at the SPE Annual Technical Conference and Exhibition held in San Antonio, Texas, U.S.A., 11 pages.

Oh, S. et al., "Pressure-Driven Suspension Flow Near Jamming", Physical Review Letters, 2015, 114, 088301, 5 pages.

Okafor, M. N. et al., "Experimental Comparison of Rheology Models for Drilling Fluids", SPE 24086, presented at the SPE Western Regional Meeting, Bakersfield, California, U.S.A., 1992, pp. 575-581.

Ong, J. T. et al., "In Well Nuclear Magnetic Resonance (NMR) Multiphase Flowmeter in the Oil and Gas Industry", SPE 89978, 2004, presented at the SPE Annual Technical Conference and Exhibition, Houston, Texas, U.S.A., 10 pages.

Perez-Perez, A. R. et al., "A statistical and graphical workflow for the analysis of magnetic susceptibility data from drill cuttings in a hydrocarbon exploration setting", Geophysics, 2016, 81(2), pp J35-J46.

Price, W. S., "Pulsed-Field Gradient Nuclear Magnetic Resonance as a Tool for Studying Translational Diffusion: Part 1. Basic Theory", Concepts in Magnetic Resonance, 1997, 9(5), pp. 329-336.

Purcell, W.R., "Capillary Pressures, Their Measurement Using Mercury and the Calculation of Permeability Therefrom", Petroleum Transactions, AIME, 1949, pp. 39-48.

Randall, B. V. et al., "Flow of Mud During Drilling Operations", SPE-9444-PA, Journal of Petroleum Technology, 1982, 34(7) pp. 1414-1420.

Rofe, C. J. et al. "Nuclear magnetic resonance imaging of apparent slip effects in xanthan solutions", Journal of Rheology, 1996, 40, pp. 1115-1128.

Romanenko, K. et al., Permeability Mapping in Naturally Heterogeneous Sandstone Cores by Magnetization Prepared Centric-Scan SPRITE, AIChE Journal, 2012, 58(12), pp. 3916-3926.

Saasen, A. et al., "Automatic Measurement of Drilling Fluid and Drill-Cuttings Properties", SPE 1126867 Drilling Completion, Dec. 2009, pp. 611-625.

Sankey, M. H. et al., "Magnetic resonance velocity imaging of liquid and gas two-phase flow in packed beds", Journal of Magnetic Resonance, 2009, 196, pp. 142-148.

Santarelli, F. J. et al., "Formation Evaluation from Logging on Cuttings", SPE-36851, SPE Reservoir Evaluation Engineering, 1998, 1(3) pp. 238-244.

Scheven, U. M. et al., "Quantitative nuclear magnetic resonance measurements of preasymptotic dispersion in flow through porous media", Physics of Fluids, 2005, 17, pp. 117107: 7 pages.

Stejskal, E. O. et al., "Spin-Diffusion Measurements: Spin Echoes in the Presence of a Time-Dependent Field Gradient", Journal of Chemical Physics, 1965, 42, pp. 288-292.

Swanson, B. F.,"A Simple Correlation Between Permeability and Mercury Capillary Pressures", Journal of Petroleum Technology, 1981, pp. 2498-2504, 1981.

Tanner, J. E., "Use of the Stimulated Echo in NMR Diffusion Studies", Journal of Chemical Physics, 1970, 52(5), pp. 2523-2526.

Thomeer, J. H. M., "Introduction of a Pore Geometrical Factor Defined by the Capillary Pressure Curve", Transacations of the AIME, 1960, pp. 73-77.

Thomeer, J. H., "Air Permeability as a Function of Three Pore Network Parameters", Transactions of the AIME, 1983, pp. 809-814.

(56) References Cited

OTHER PUBLICATIONS

Timur, A.,"Effective Porosity and Permeability of Sandstones Investigated Through Nuclear Magnetic Resonance Principles", Paper presented at the SPWLA Ninth Annual Logging Symposium, Jun. 23-26, 1968, 18 pages.

Tonner, D. et al.,"Automation Provides Unique Insights of the Rock Record and Subsurface Through the Delivery of a Robotic Sample Collection and Analysis Device", IADC/SPE-189680-MS, 2018, presented at the IADC/SPE Drilling Conference and Exhibition held in Fort Worth, Texas, U.S.A., 12 pages.

Vajargah, A. K. et al., "Automated Drilling Fluid Rheology Characterization with Downhole Pressure Sensor Data", SPE/IADC-173085-MS, presented at the SPE/IADC Drilling Conference and Exhibition, London, England, 2015, 22 pages.

Van Oort, E. et al. "Automated Drilling Fluid Analysis Using Advanced Particle Size Analyzers", IADC/SPE-178877-MS, presented at the 2016 IADC/SPE Drilling Conference and Exhibition held in Fort Worth, Texas, U.S.A., 27 pages.

Venkataramanan, L. et al., "Solving Fredhold integrals of the first kind with tensor product structure in 2 and 2.5 dimensions, IEEE Transactions on Signal Processing", 2002, 50(5), pp. 1017-1026.

Waggoner, R. A. et al., "Velocity Distribution of Slow Fluid Flows in Bentheimer Sandstone: An NMRI and Propagator Study", Magnetic Resonance Imaging, 1996, 14(9), pp. 1085-1091.

Washburn, K.E et al., "The dependence on magnetic field strength of correlated internal gradient relaxation time distributions in heterogeneous materials", Journal of Magnetic Resonance, 2008, 194(1), pp. 33-40.

Yoon, W. B. et al., "Rheology of Yogurt During Pipe Flow as Characterized by Magnetic Resonance Imaging", Journal of Texture Studies, 2002, 33(5), pp. 431-444.

Krohne, M-Phase 5000, Magnetic resonance multiphase flowmeter for simultaneous measurement of oil, gas and water, from website: https://krohne.com/en/products/archived-products/m-phase-5000. 2015, 5 pages.

SLB, Zhaikmunai Saves Drilling Days, Enhances Lithology Identification Using StingBlade Bit, Case Study, from website: https://www.slb.com/resource-library/case-study/bdt/stingblade-nostrum-cs, 2014, 13 pages.

Cayeux, E. et al., "Use of a Transient Cuttings Transport Model in the Planning, Monitoring and Post Analysis of Complex Drilling Operations in the North Sea", IADC/SPE-178862-MS, presented at the IADC/SPE Drilling Conference and Exhibition held in Fort Worth, Texas, 2016, 20 pages.

Ibrahim, M. A. et al., "Learnings from Spectral GR Measurements from LWD and from Cuttings in High and Low Angle Wells", presented at the SPWLA 62nd Annual Logging Symposium, 2021, 8 pages.

OFITE 50-mL retort kit instruction manual, Ver 6.0, 2015, Updated Mar. 17, 2023, OFI Testing Equipment, Inc., Houston, TX, 17 pages.

\* cited by examiner

SYSTEMS AND METHODS FOR DETERMINING THE MINERALOGY OF DRILL SOLIDS

CROSS-REFERENCE TO RELATED APPLICATIONS

This application claims the benefit of, and priority to, U.S. Patent Application No. 63/265,228, filed Dec. 10, 2021, and to Indonesian Patent Application No. P00202112335, filed Dec. 30, 2021, which applications are expressly incorporated herein by this reference in their entireties.

BACKGROUND

Wellbores may be drilled into a surface location or seabed for a variety of exploratory or extraction purposes. For example, a wellbore may be drilled to access fluids, such as liquid and gaseous hydrocarbons, stored in subterranean formations and to extract the fluids from the formations. A variety of drilling methods may be utilized depending partly on the characteristics of the formation through which the wellbore is drilled.

For instance, in drilling a well, a fluid known as drilling mud may be pumped through the downhole tool to aid in the drilling process. The drilling mud exits the drill bit and is used to lubricate and cool the cutting elements on the drill bit. As the cutting elements degrade the rock formation, rock cuttings are formed. The drilling mud may also be used to transport the rock cuttings to surface. At the surface, the drilling mud passes over a shaker table and rock cuttings are removed to allow the drilling mud to be recycled and reused in the drilling process.

SUMMARY

In some embodiments, a method for measuring at least one property of a sample from a wellbore includes obtaining a sample of fluid including at least fines from a downhole environment, exposing the sample to a magnetic field, measuring a magnetic susceptibility of the fines in the sample in response to the magnetic field, and identifying at least one mineral present in the fines based at least partially on the magnetic susceptibility.

In some embodiments, a method of measuring material from a wellbore includes obtaining at least one sample of fluid including at least fines from a downhole environment, exposing the at least one sample to a magnetic field in an NMR device, measuring a magnetic susceptibility contrast of the fines in the at least one sample in response to the magnetic field, identifying a concentration of at least one mineral present in the fines based at least partially on the magnetic susceptibility contrast, comparing the concentration of the at least one mineral to a mineralogy log of the downhole environment, and determining a provenance of the fines in the downhole environment.

In some embodiments, a method of measuring material from a wellbore includes obtaining at least one sample of fluid including fines and cuttings from a downhole environment, measuring at least one property of the fines in the at least one sample and thereby collecting a fines value, creating a log of fines values for the at least one property, comparing the log of fines values to the log of cuttings values, and depth matching the fines and the cuttings.

This summary is provided to introduce a selection of concepts that are further described below in the detailed description. This summary is not intended to identify key or essential features of the claimed subject matter, nor is it intended to be used as an aid in limiting the scope of the claimed subject matter.

Additional features and aspects of embodiments of the disclosure will be set forth in the description which follows, and in part will be obvious from the description, or may be learned by the practice of such embodiments. The features and aspects of such embodiments may be realized and obtained by means of the instruments and combinations particularly pointed out in the appended claims. These and other features will become more fully apparent from the following description and appended claims or may be learned by the practice of such embodiments as set forth hereinafter.

BRIEF DESCRIPTION OF THE DRAWINGS

In order to describe the manner in which the above-recited and other features of the disclosure can be obtained, a more particular description will be rendered by reference to specific embodiments thereof which are illustrated in the appended drawings. For better understanding, the like elements have been designated by like reference numbers throughout the various accompanying figures. While some of the drawings may be schematic or exaggerated representations of concepts, non-schematic drawings should be considered as being to scale for some embodiments of the present disclosure, but not to scale for other embodiments contemplated herein. Understanding that the drawings depict some example embodiments, the embodiments will be described and explained with additional specificity and detail through the use of the accompanying drawings in which.

DETAILED DESCRIPTION

Figure 1:
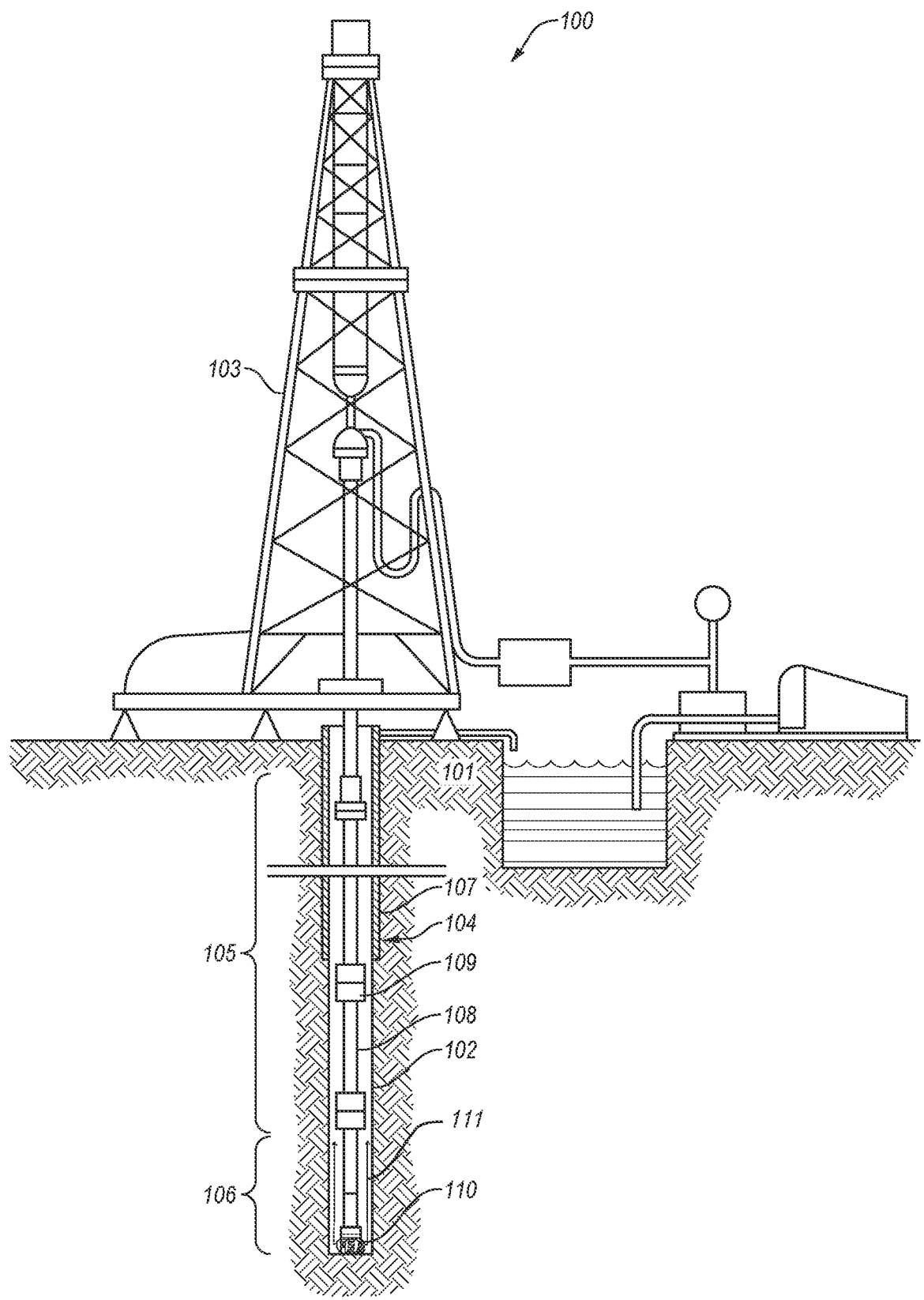
FIG. 1 is a side schematic view of a drilling system, according to some embodiments of the present disclosure.

Embodiments of the present disclosure generally relate to devices, systems, and methods for analyzing drill solids in a drilling fluid. More particularly, some embodiments of the present disclosure relate to the bulk measurement of fines in drilling fluid to measure at least one property of the fines and determine the mineralogy thereof. In some embodiments, a magnetic susceptibility of the fines is measured using a nuclear magnetic resonance (NMR) spectrometer. The magnetic susceptibility is a measurement of the degree of magnetization of a material in response to an applied magnetic field. After the NMR spectrometer applies a magnetic field, the induced magnetic field of the sample is measured. In some embodiments, the induced magnetic field is measured by measuring a response to a radio frequency probe. The contrast between the liquid medium of the sample and the particles in the liquid medium provides information regarding the composition of the sample.

A sample of liquid-saturated porous material, or wet powder, can be placed in the magnetic field for measurement. An assumption can be made that the magnetic field is homogeneous and does not influence the measurement of liquid relaxation time. However, the solid-liquid magnetic susceptibility contrast in porous media or wet powders alters the static homogeneous magnetic field of the NMR instrument on the scale of the pores (or inter-particle voids). This results in line broadening. Line broadening is observed when the relaxation time of the material in the sample is dominated by the local magnetic field inhomogeneity (so-called "internal gradients") rather than the surface relaxivity, so the observed NMR spectral line (Fourier inverse of relaxation time) broadens. The degree of line broadening is determined by the apparent magnetic susceptibility contrast $\Delta\chi_{app}$ of the solid and liquid portions and the strength of the static magnetic field $B_0$ according to Equation 1

$$\Delta\chi_{app} = \frac{\gamma B_0}{T_2^*} \quad (1)$$

where $\gamma$ is the gyromagnetic ratio of the spin under observation (typically $^1H$) in the NMR spectrometer, and $T_2^*$ is the transverse relaxation time due to the local magnetic field inhomogeneity. A longitudinal relaxation time $T_1$ is not present in the relationship and, thus, is insensitive to the magnetic susceptibility-induced internal gradients.

The NMR magnetic susceptibility contrast $\Delta\chi_{app}$ can be modified from the true magnetic susceptibility contrast $\Delta\chi = \chi_{rock} - \chi_{liquid}$ due to the influence of pore size on the local magnetic field distortions. For example, the NMR magnetic susceptibility contrast $\Delta\chi_{app}$ can be modified if the pores are very large (>100 μm) or very small (<0.1 μm), or if the liquid-solid magnetic susceptibility contrast is very small. In many subsurface rocks, the magnetic susceptibility contrast between mineral and brine or oil is modest to large, and is appropriate for analysis at static magnetic field strengths available on commercial laboratory bench-top NMR spectrometers (e.g., <0.5 Tesla (T)). The NMR apparent magnetic susceptibility measurements will be interpreted as an NMR mineralogy log. The results may be plotted in a conventional well log format for comparison to downhole logs.

In the present disclosure, fines are drilling solids that are transported in the drilling fluid substantially in suspension. The fines, therefore, are transported by the drilling fluid at the flowrate of the drilling fluid, which is in contrast to drill cuttings which are larger and fall out of the suspension in the drill fluid. Due to not being in suspension, the drill cuttings are transported through the wellbore to the surface for analysis at a rate that is slower than the flowrate of the drill fluid. In some embodiments, measurement and comparison of the minerology of fines and cuttings allows accurate depth matching of the cuttings.

NMR magnetic susceptibility is a bulk measurement technique that is suitable for fines analysis. The NMR magnetic susceptibility can provide accurate mineralogy measurements in bulk samples to provide sufficient statistics for mineralogical analysis.

FIG. 1 shows one example of a drilling system 100 for drilling an earth formation 101 to form a wellbore 102. The drilling system 100 includes a drill rig 103 used to turn a drilling assembly 104 which extends downward into the wellbore 102. The drilling assembly 104 may include a drill string 105 and a bottomhole assembly (BHA) 106 attached to the downhole end of drill string 105. Where the drilling system 100 is used for drilling formation, a drill bit 110 can be included at the downhole end of the BHA 106.

The drill string 105 may include several joints of drill pipe 108 a connected end-to-end through tool joints 109. The drill string 105 transmits drilling fluid through a central bore and can transmit rotational power from the drill rig 103 to the BHA 106. In some embodiments, the drill string 105 may further include additional components such as subs, pup joints, etc. The drill pipe 108 provides a hydraulic passage through which drilling fluid 111 is pumped from the surface. The drilling fluid 111 discharges through selected-size nozzles, jets, or other orifices in the bit 110 for the purposes of cooling the bit 110 and cutting structures thereon, for lifting cuttings out of the wellbore 102 as it is being drilled, and for preventing the collapse of the wellbore 102. The drilling fluid 111 carries drill solids including drill fines, drill cuttings, and other swarf from the wellbore 102 to the surface. The drill solids can include components from the earth formation 101, the drilling assembly 104 itself, from other man-made components (e.g., plugs, lost tools/components, etc.), or combinations thereof.

The BHA 106 may include the bit 110 or other components. An example BHA 106 may include additional or other components (e.g., coupled between to the drill string 105 and/or the bit 110). Examples of additional BHA components include drill collars, stabilizers, measurement-while-drilling (MWD) tools, logging-while-drilling (LWD) tools, downhole motors, underreamers, directional steering tools, section mills, hydraulic disconnects, jars, vibration or dampening tools, other components, or combinations of the foregoing. In some examples, an MWD and/or LWD can include magnetic measurement tools; however, conventional downhole NMR tools and other magnetic measurement tools can lack a static magnetic field that is sufficiently uniform to enable a measure of the spectral line width, as used in the systems and methods described herein.

In general, the drilling system 100 may include other drilling components and accessories, such as special valves (e.g., kelly cocks, blowout preventers, safety valves, centrifuges, shaker tables, and rheometers). Additional components included in the drilling system 100 may be considered a part of the surface system (e.g., drill rig 103, drilling assembly 104, drill string 105, or a part of the BHA 106, depending on their locations and/or use in the drilling system 100).

The bit 110 in the BHA 106 may be any type of bit suitable for degrading downhole materials. For instance, the bit 110 may be a drill bit suitable for drilling the earth formation 101. Example types of drill bits used for drilling earth formations are fixed-cutter or drag bits, roller cone bits, impregnated bits, or coring bits. In other embodiments, the bit 110 may be a mill used for removing metal, composite, elastomer, other materials downhole, or combinations thereof. For instance, the bit 110 may be used with a whipstock to mill into casing 107 lining the wellbore 102. The bit 110 may also be a junk mill used to mill away tools, plugs, cement, other materials within the wellbore 102, or combinations thereof. Swarf or other cuttings formed by use of a mill may be lifted to surface by the drilling fluid 111 or may be allowed to fall downhole.

In some embodiments, a drilling system 100 or field laboratory (optionally at the drilling site) includes an NMR spectrometer. A sample of the drilling fluid 111 received at the surface is collected, and the sample is placed in the NMR spectrometer. The NMR spectrometer applies a magnetic field to the sample, including the drilling fluid and the solids suspended and/or contained therein. The magnetic field induces a magnetization of the components of the sample. In some embodiments, the NMR spectrometer may be part of a rheometer device, and analysis is optionally automated.

Figure 2:
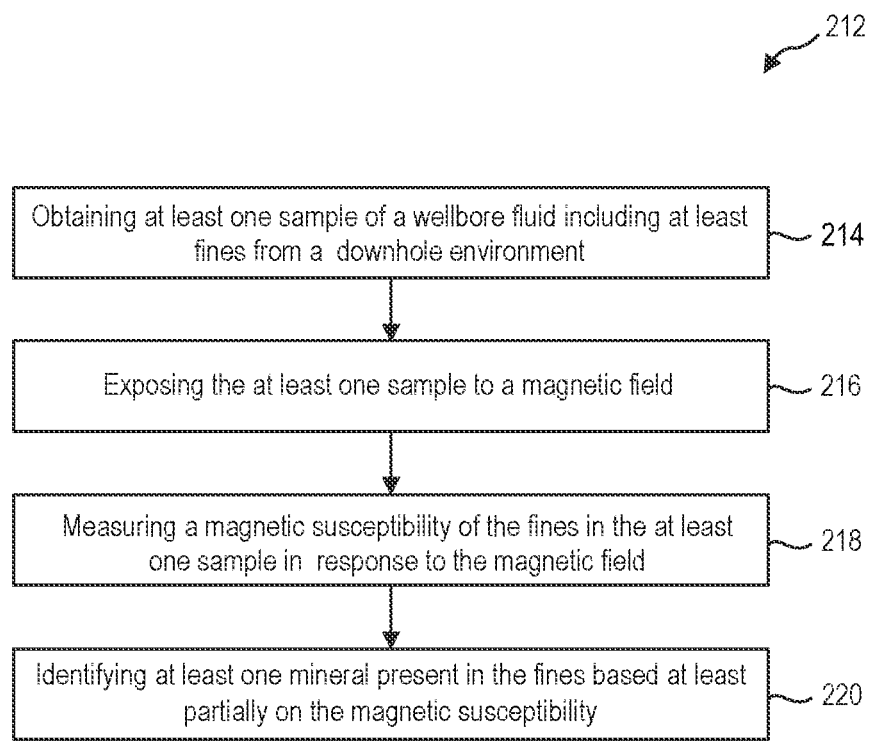
FIG. 2 is a flowchart illustrating a method of measuring at least one property of a sample, according to some embodiments of the present disclosure.

FIG. 2 is a flowchart illustrating an example method 212 of measuring at least one property of the of drilling fluid samples. In some embodiments, the method 212 includes obtaining at least one sample of a fluid including at least fines from a downhole environment at 214. The fluid may include various components, including drilling fluid (e.g., drilling mud) and produced fluids.

As described herein, fines are particles that are suspended in the fluid. The fines can have an average or median size up to 0.3 mm or up to 0.5 mm in size. In some examples, the fines have an average or median diameter of up to 0.3 mm or up to 0.5 mm. In some examples, the fines have an average or median major axis up to up to 0.3 mm or up to 0.5 mm. In some examples, an average between a major axis and a minor axis of the fines is up to 0.3 mm or up to up to 0.5 mm. In some embodiments, fines may be larger than 0.5 mm. For instance, the diameter, major diameter, or average between the major and minor diameter may be up to 0.6 mm, 0.7 mm, 0.75 mm, 0.8 mm, 0.9 mm, 1.0 mm, or values therebetween.

In some embodiments, the one or more samples further include cuttings. As described herein, the cuttings are particles larger than the fines, and which fall out of suspension in fluid. The cuttings can be between 1 and 3 mm in size. In some examples, the cuttings have an average or median diameter between 1 and 3 mm. In some examples, the average or median major axis of the cuttings is between 1 and 3 mm. In some examples, an average of the major axis and the minor axis of the cuttings is between 1 and 3 mm. In other embodiments, cuttings may be larger than 3 mm. For instance, the diameter, major diameter, or average between the major and minor diameter may be greater than 3 mm (e.g., up to 4 mm, 5 mm, 6 mm, 7 mm, 8 mm, 9 mm, 10 mm, or values therebetween). In some embodiments, the size of fines and cuttings may vary. For instance, depending on the composition of the fines and cuttings, or the properties of the fluid (e.g., composition, viscosity, or density), different sizes of particles may be in suspension or fall out of suspension.

Obtaining the sample(s) from the downhole environment includes, in some embodiments, collecting the sample(s) from fluid at the surface of the wellbore. In some embodiments, obtaining the sample includes collecting sample(s) of drilling fluid after the drilling fluid has passed over, through, or around a ditch magnet that removes ferrous and/or ferromagnetic material. In some embodiments, obtaining the sample(s) includes filtering a portion of the fluid to remove at least some particles larger than the fines. For example, the fines and cuttings may be at least partially separated at a shaker table. In some embodiments, obtaining the sample(s) includes collecting the sample or samples from the shaker table.

In contrast to cuttings which are carried by, but not suspended in, the drilling fluid, the fines are suspended in the drilling fluid. In some embodiments, the drilling fluid is an oil-based drilling fluid (e.g., true oil-based drilling fluid, synthetic-based drilling fluid, or invert emulsion drilling fluid). In some embodiments, the drilling fluid is a water-based drilling fluid. In some embodiments, methods include separating the fines and cuttings to allow independent analysis of the fines and the cuttings. In some embodiments, the sample(s) include both the fines and cuttings during analysis. In some embodiments, a sample is rinsed to remove certain fluids (e.g., drilling fluid) and optionally contains a different liquid medium, such as water, an oil-based fluid, solvent, or other liquid.

In some embodiments, at least a portion of the fluid of the original sample(s) is removed from the sample(s). For example, the sample(s) may be prepared by filtering of the fines and/or cuttings from the fluid. In some examples, the sample(s) may be prepared by centrifugation. Centrifugation of the sample(s) may provide minimal excess liquid in the sample(s), while some liquid remains in the sample(s).

In the illustrated embodiment, the method 212 further includes exposing the sample(s) to a magnetic field. In some embodiments, the magnetic field has a magnitude in a range having an upper value, a lower value, or upper and lower values including any of 0.1 T, 0.2 T, 0.3 T, 0.4 T, 0.5 T, or any value therebetween. In some examples, the magnetic field has a magnitude less than 0.5 T. In some examples, the magnetic field has a magnitude greater than 0.1 T. In some examples, the magnetic field has a magnitude between 0.1 T and 0.5 T. In some examples, the magnetic field has a magnitude between 0.3 T and 0.5 T. In still other example embodiments, the magnitude of the magnetic field may be less than 0.1 T or greater than 0.5 T.

In some embodiments, a bench top NMR instrument is used at the rig site or another location. A 0.5 T magnetic field corresponds to a 20 MHz resonant frequency for $^1$H and such a magnitude is possible in a bench-top device. In some embodiments, the magnetic field is adjustable. For instance, a combination of mechanical and electric shims can provide a uniform static magnetic field. In some embodiments, the magnetic field has a line width of better than 5 parts per million (ppm) full-width, half-maximum (FWHM) on a bulk water sample.

In some embodiments, the magnetic field is produced by an NMR spectrometer. The method 212 can include measuring a magnetic susceptibility of the fines in the sample(s) in response to the magnetic field at 216. The magnetic field induces a magnetization in the components of a sample, which may then be measured by the NMR spectrometer. The magnetization and resulting magnetic field produced by the components of the sample will vary depending on the composition and proportions of the components of the sample. For example, a negative magnetic susceptibility corresponds to a diamagnetic component and a positive magnetic susceptibility corresponds to a paramagnetic component.

The method 212 further includes, in some embodiments, identifying at least one mineral or other material present in the fines based at least partially on the magnetic susceptibility at 218. In some embodiments, the magnetic susceptibility is compared to a mineralogy log of the formation. The mineralogy log optionally includes magnetic susceptibility and/or magnetic permeability values for the known or expected minerals or layers of the formation (such as earth formation 101 of FIG. 1). In other embodiments, a separate reference may provide the magnetic susceptibility and/or magnetic permeability values for the known or expected minerals or layers of the formation. The magnetic susceptibility can be correlated to at least one mineral or layer of the mineralogy log to identify the mineral based at least partially on the magnetic susceptibility.

Figure 3:
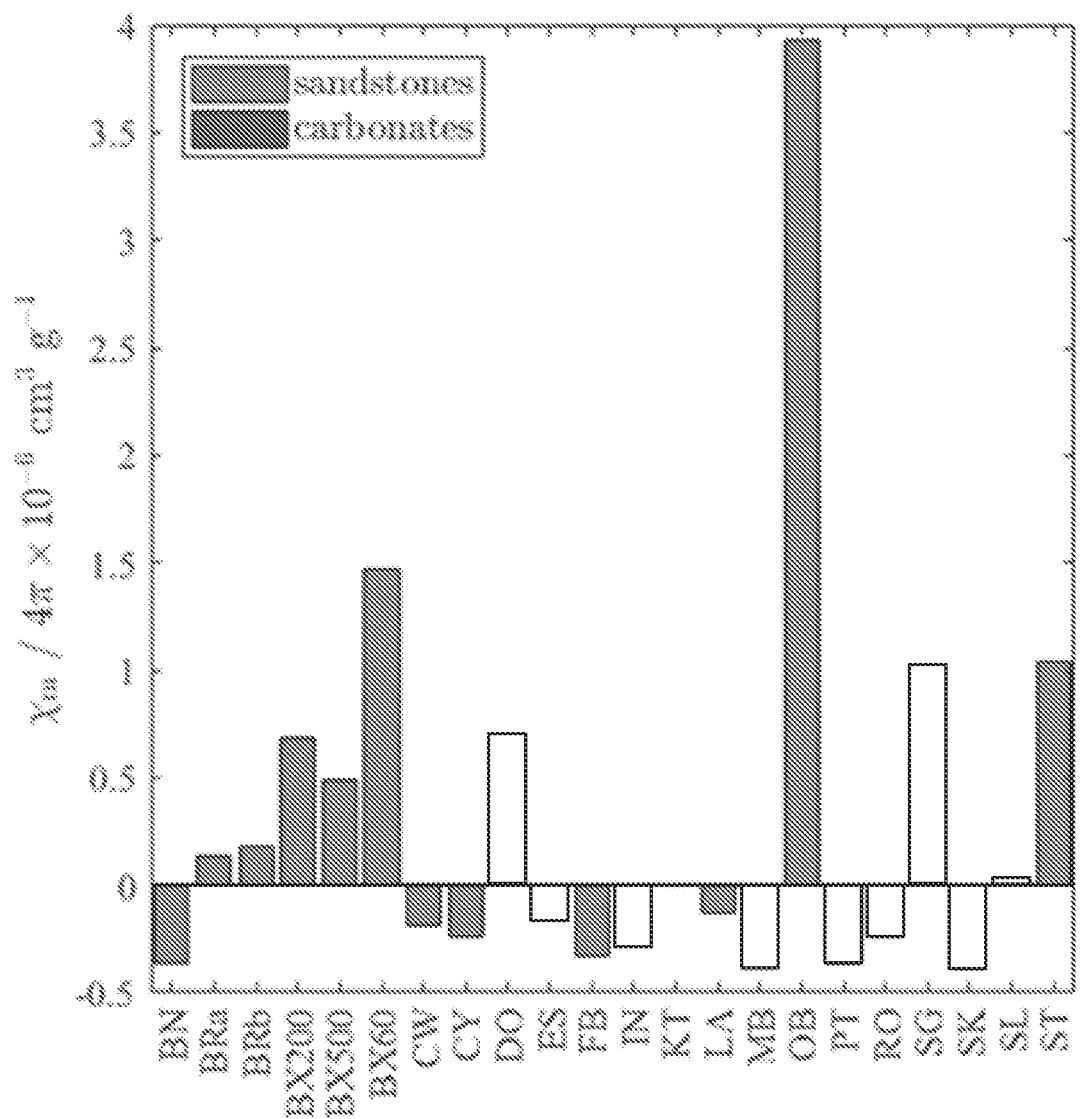
FIG. 3 is a graph illustrating magnetic susceptibility for different rock formations, according to some embodiments of the present disclosure.

FIG. 3 is a graph illustrating the magnetic susceptibility of outcrop rocks. Outcrop rocks are rocks proximate a hydrocarbon reservoir that are not and/or have not been in contact with the hydrocarbons stored in the reservoir. The outcrop rocks generally have low magnetic susceptibilities compared with typical reservoir formations that contain hydrocarbons, but the outcrop rocks illustrate a positive correlation between the measured magnetic susceptibility and the iron oxide content obtained from chemical analysis of the mineral composition. The correlation is weaker in samples with low iron content, such as diamagnetic samples. In some subsurface formations, iron is the main contributor to the measured magnetic susceptibility. As such, some samples may be prepared by removal of ferrous materials by ditch magnet or other removal mechanism to limit or even prevent the magnetic susceptibility signal from being dominated by the presence of iron-rich particles.

Figure 4:
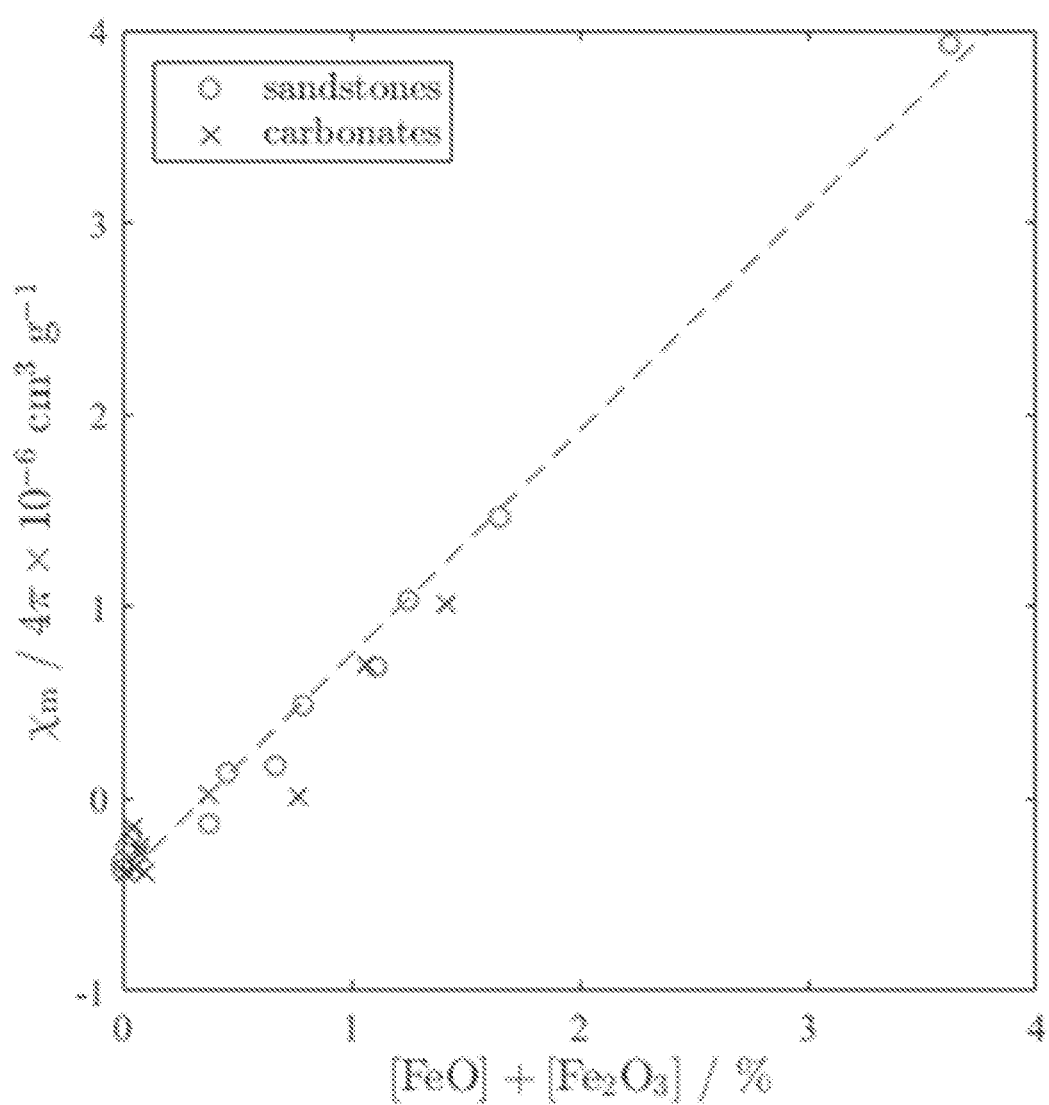
FIG. 4 is a graph showing the relationship of magnetic susceptibility measurements relative to iron oxide concentration in a sample, according to some embodiments of the present disclosure.

FIGS. 4-7 are graphs that represent testing performed to confirm the correlation of magnetic susceptibility to chemical composition of samples. FIG. 4 illustrates a correlation between mass magnetic susceptibilities and iron oxide content. The mass magnetic susceptibility is on the y-axis, and the iron oxide (both FeO and $Fe_2O_3$) content is on the x-axis. As the iron oxide content increases, the mass magnetic susceptibility increases in a strong correlation.

The experimental correlation was obtained through NMR measurements performed on a 12.9 MHz magnet, and the magnetic susceptibility contrast was obtained from a free induction decay (FID) measurement of each sample. FID measurement uses a single radio frequency (RF) excitation pulse followed by an observation interval of approximately 10 milliseconds (ms). The observed signal decays at a rate determined by the local environment of the excited spins (e.g., $^1H$). In some embodiments, at low magnetic field strengths, the local environment in the sample is dominated by variations (i.e., inhomogeneities) and gradients in the internal magnetic field generated by the magnetic susceptibility contrast between components. The variations lead to the line broadening described herein. The signal decays are fitted by a single exponential function to obtain the $T_2^*$ relaxation time for each sample. The magnetic susceptibility contrast was calculated using eq (1) described herein.

Figure 5:
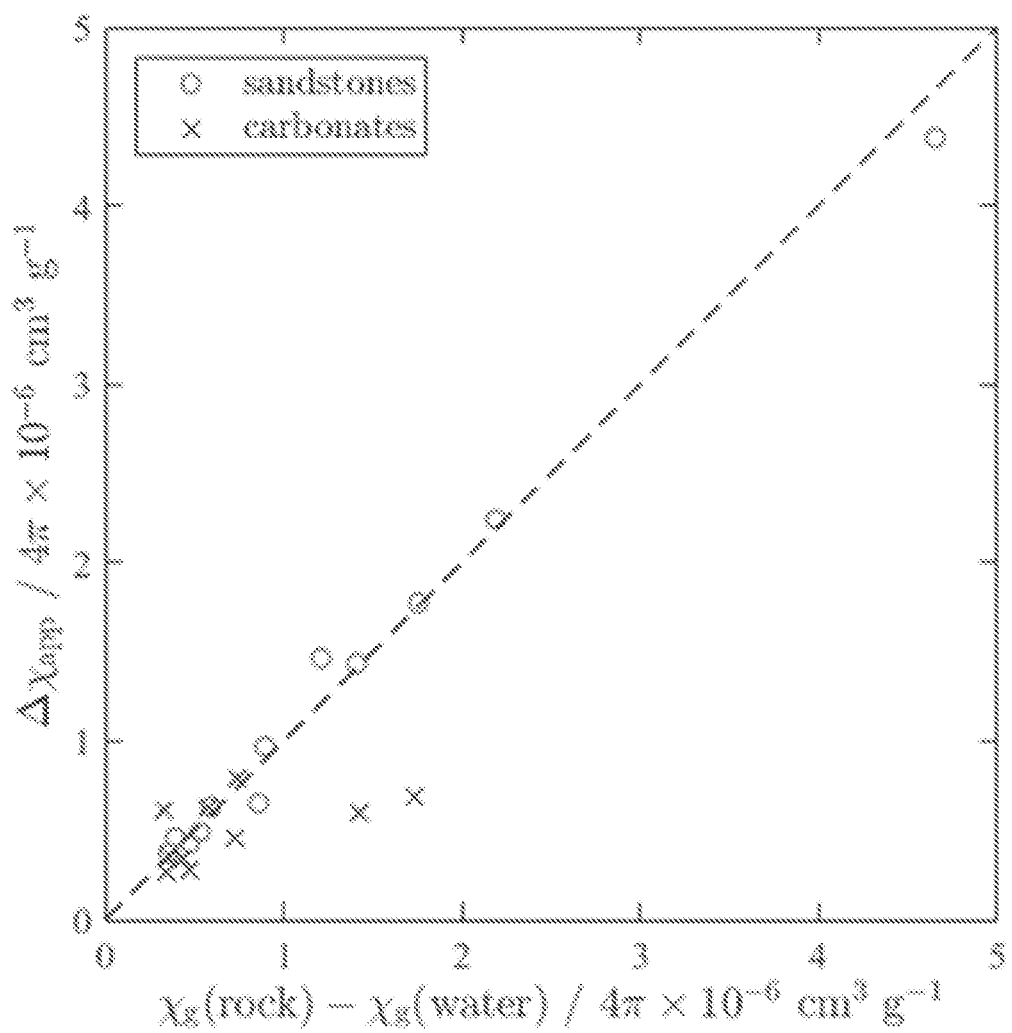
FIG. 5 is a graph comparing apparent magnetic susceptibility measurements collected according to some embodiments of the present disclosure relative to a conventional measurement.

FIG. 5 is a graph illustrating a comparison between NMR apparent magnetic susceptibility measured according to at least one embodiment of the present disclosure and conventional Gouy balance measurement of wet rock powders. Except for two obvious carbonate formation outliers—namely Doulting (DO) and Stoke Ground (SG) limestones—the NMR measurement of susceptibility agrees well with the conventional measurement and can monitor changes in the rock mineralogy during drilling.

Figure 6:
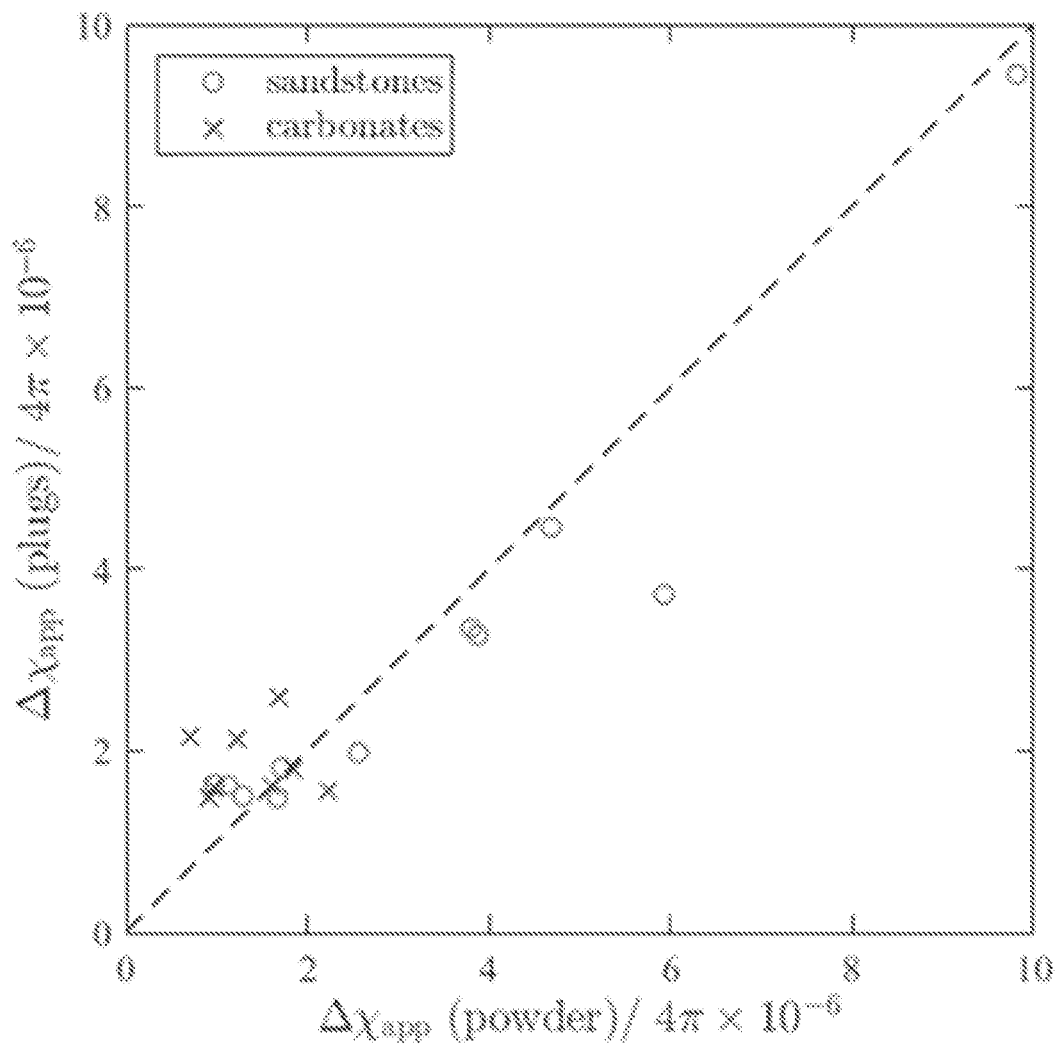
FIG. 6 is a graph illustrating a comparison of apparent magnetic susceptibility measurements for powder samples and core-plug samples of the same origin, according to some embodiments of the present disclosure.

As described in relation to FIG. 2, a method of analyzing a sample according to the present disclosure can include different sample preparations. FIG. 6 is a graph illustrating the correlation between apparent magnetic susceptibilities of wet powder samples and brine-saturated core-plugs. The wet powder samples were measured using a RF probe with a 23 mm bore. The brine-saturated core-plugs were measured using a RF probe with a 53 mm bore. The static magnetic field was adjusted by a combination of mechanical and electric shims to achieve a spectral line width for bulk water better than 10 ppm FWHM. In some embodiments, the natural line width of the magnet (when measuring a bulk liquid calibration sample) may be as small as practically achievable to provide sensitivity to the line-broadening caused by the introduction of the rock minerals (which introduces the internal gradients).

For the measurements used in FIG. 6, the rock powders (approx. 10 g each) were suspended in deionized water and then centrifuged at 500 revolutions per minute (RPM) for 60 minutes to achieve a dense, wet slurry. In some embodiments, a sample is centrifuged at a greater or lesser rotational speed and/or for a greater or lesser duration. In the example embodiment, the excess liquid was aspirated from the centrifuge tubes and the sealed centrifuge tubes were placed directly in the NMR magnet. An FID measurement was acquired for each sample. Each measurement included 32 repeat scans to improve the signal to noise ratio (SNR) and accommodate the RF phase cycle. A repeat delay of 10 seconds was allowed between each scan to ensure full polarization of the spin ensemble. Each FID included 8192 data points, each with a dwell time of 10 microseconds (μs). A fluorine-suppression digital filter was used to prevent signal contamination from PTFE components in the probe body.

The core-plugs measured for the comparison illustrated in FIG. 6 were saturated in low-salinity brine. The core-plugs were subsequently wiped on a non-porous plastic film to remove surface water, then wrapped in plastic film for the duration of the measurement. The same NMR protocol was applied to the powders and plugs.

The magnetic susceptibility was slightly different for the deionized water and brine used in the wet powder samples and the core-plug samples, respectively, for NMR measurement. A small offset is observed between the measurements of the wet powder samples and the core-plug samples related to the different liquid media (the DI water and the brine). The difference between the liquids is relatively small compared to the solid/liquid contrast. However, water is diamagnetic. In samples where the rocks are diamagnetic, the contrast can be near to zero.

Figure 7:
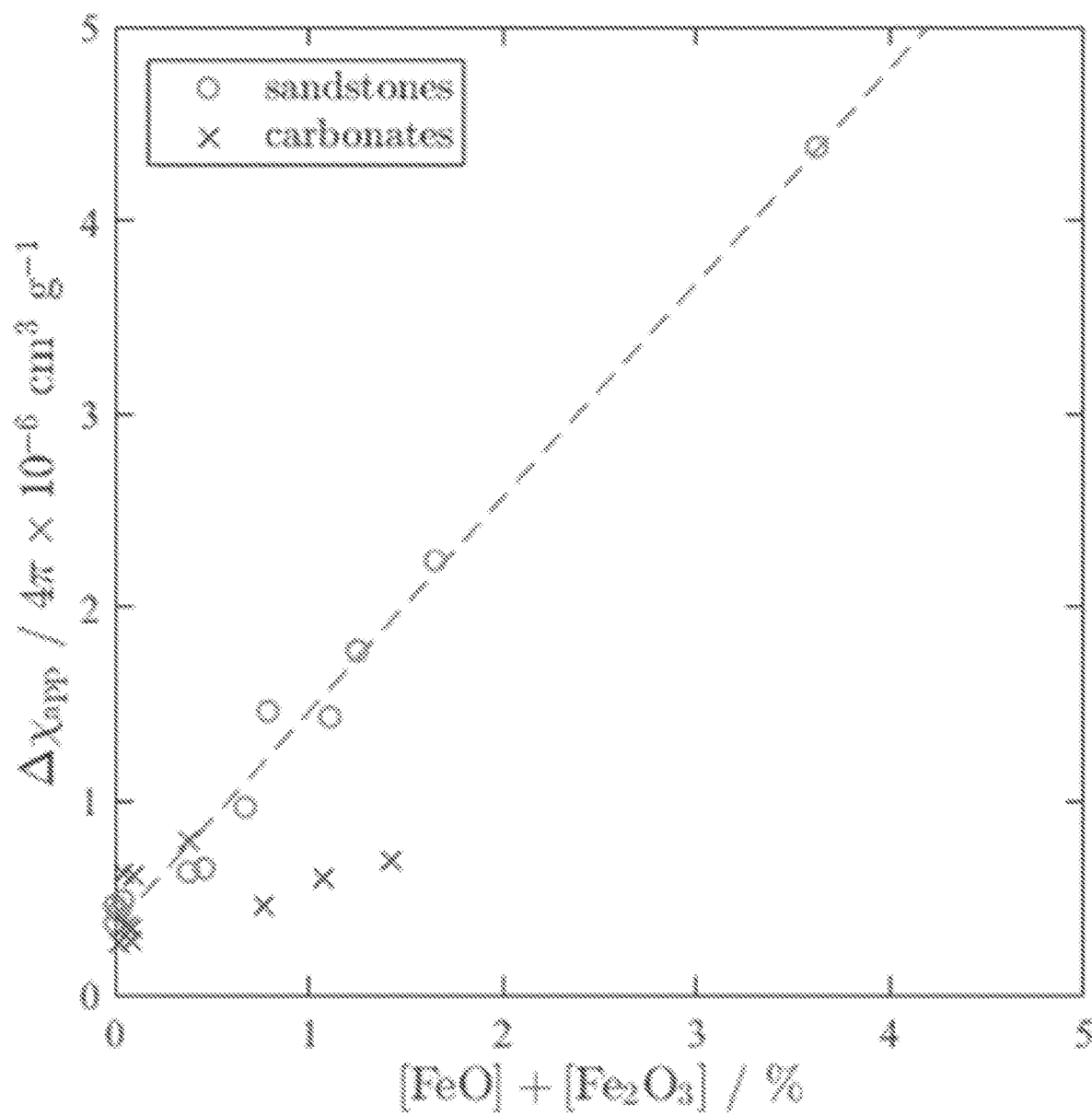
FIG. 7 is a graph illustrating a comparison of apparent magnetic susceptibility contrast of powdered sandstones and the known iron content of the formations, according to some embodiments of the present disclosure.

FIG. 7 is a comparison of NMR apparent magnetic susceptibility contrast of powdered sandstones and the known iron content of the formations. The magnetic susceptibility of a subsurface sample is related to the quantity of paramagnetic material in the sample by the Curie law as stated in Equation 2:

$$\chi = \frac{[M]N_A}{MW_M} \times \frac{\mu_0(n_B\mu_B)^2}{3kT} \quad (2)$$

where M is the magnetization of the material, $N_A$ is the Avogadro constant, WM is molar weight, k is the Boltzmann constant, T is the temperature in Kelvin, $\mu_0$ is the permeability of free space, $n_B$ is the quantity of magnetic atoms per unit volume of the material, and $\mu_B$ is the Bohr magneton.

In some embodiments, NMR measurements as described herein are performed in under 1 minute, allowing the magnetic susceptibility of the components of the sample to be measured substantially continuously from the fluid that is received at the surface during drilling operations. The continuous measurements of samples can allow a near-real-time assay of the earth formation during drilling. Where the drilling fluid flowrate is relatively constant, the depth from which the fines are received can generally be calculated based on the flow velocity through the wellbore.

Mineralogy from subsurface material can be stored and correlated against downhole logs or drilling data (mechanical performance of the drill string). In some embodiments, the results are plotted as a log and used at least partially as a basis for decisions on directional drilling, hole cleaning, or production by identifying producible reservoir intervals.

In some embodiments, mineralogy from drill fines is correlated against concurrent analysis of drill cuttings. The arrival time of the fines at surface will be predictable based on the mud flow rate (measured independently at surface). The correlation of fines and cuttings mineralogy will enable accurate depth matching of the cuttings irrespective of the slower transport rate of the cuttings. As the transport rate of the cuttings can be relatively constant for the cuttings, the delay in transport to the surface may also be approximately constant, once determined.

Figure 8:
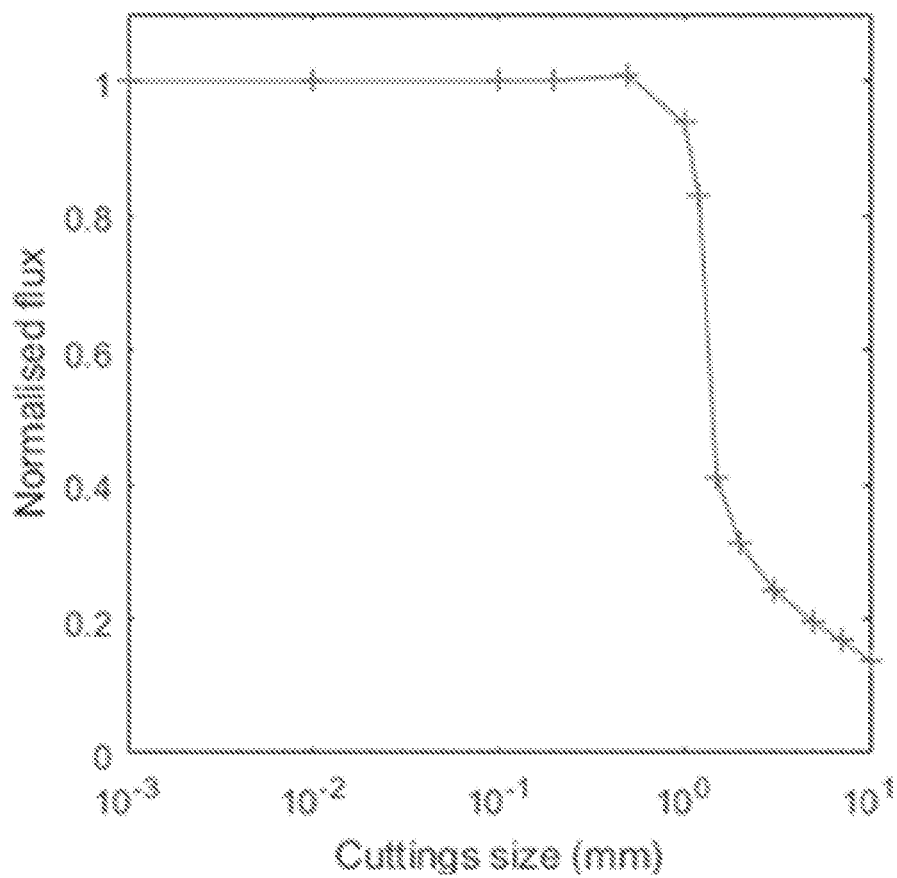
FIG. 8 is a graph showing simulation results of normalized flux for drill solids based on particle size, according to some embodiments of the present disclosure.

FIG. 8 is a graph of a simulation of drill solids transport in a horizontal wellbore. The simulation assumes an 8.5-inch borehole with a 4.5-inch diameter drill pipe that is centered in the borehole and rotating at 80 RPM. The simulation assumes a 400 gallon per minute (1500 liters per minute) circulation rate of the drilling fluid, which has a mud weight of 11 pounds per gallon (1.3 kg per liter). The fluid has a viscosity of 0.1 Pascal-seconds.

FIG. 8 illustrates the suspension of the drill fines below approximately 0.5 mm in size, which transport at normalized flux of substantially 1.0. The normalized flux is the average in the wellbore cross-section of the solids volume fraction multiplied by the local particle velocity, divided by the nominal average solids volume fraction multiplied by the average fluid velocity. A normalized flux of 1.0 indicates that the drill solids of that size are transported at the rate of the fluid velocity. At approximately 1.0 mm in cutting size, the normalized flux decreases rapidly, indicating the cuttings larger than the drill fines are transported at a lower rate in a horizontal wellbore.

Figure 9:
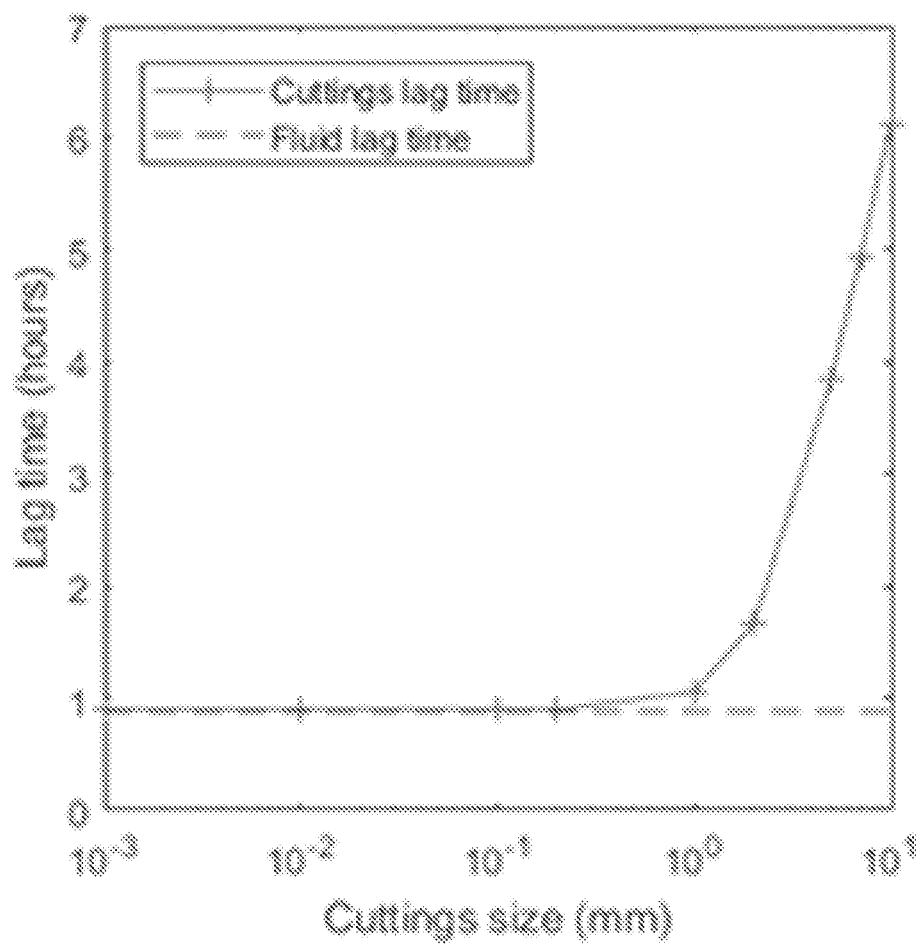
FIG. 9 is a graph showing simulation results of transport lag of drill solids based on particle size, according to some embodiments of the present disclosure.

FIG. 9 reflects this reduction in transport rate of larger cuttings. FIG. 9 is a chart illustrating the difference in transport time based on cutting size relative to a known fluid velocity. The simulation of FIG. 9 assumed a well with a trajectory vertical to 2500 feet (760 m), turning to horizontal at 6 degrees per 100 feet (6 degrees per 30 m), and finally with a horizontal section of 6000 feet (1830 m). The simulation assumed continuous drilling at 150 feet per hour (45 m per hour). Other parameters of the drilling tool and drilling fluid the same as in the previous example described in relation to FIG. 8. The simulation approximates that the drilling fluid exhibits a 1 hour duration of flow before arriving at the surface.

The drill fines below 0.5 mm in size, which were simulated as suspended in the fluid and transported at the rate of the fluid velocity, arrive substantially at the same time the drilling fluid after one hour. As cutting size increases, the lag increases. Cuttings with an average 10 mm size are calculated to arrive at the surface at 6 hours, which is 5 hours after the drilling fluid in which the cuttings were initially made.

In some embodiments, cuttings analysis provides insight to enable preventative intervention to eliminate build-up of cuttings beds that reduce the drilling efficiency. In some embodiments, compositional analysis of drill solids concentration and mineralogical composition provides formation evaluation information and input data for mud engineering process control. Cutting analysis can provide geometry, mineralogy, lithology, porosity, and permeability information. For at least the reasons stated herein, cuttings are not transported at the drilling fluid flowrate and, particularly in deviated and horizontal bores, may be transported at inconsistent rates. Cutting analysis, therefore, can benefit from accurate depth matching to produce the most useful and efficient analysis.

Figure 10:
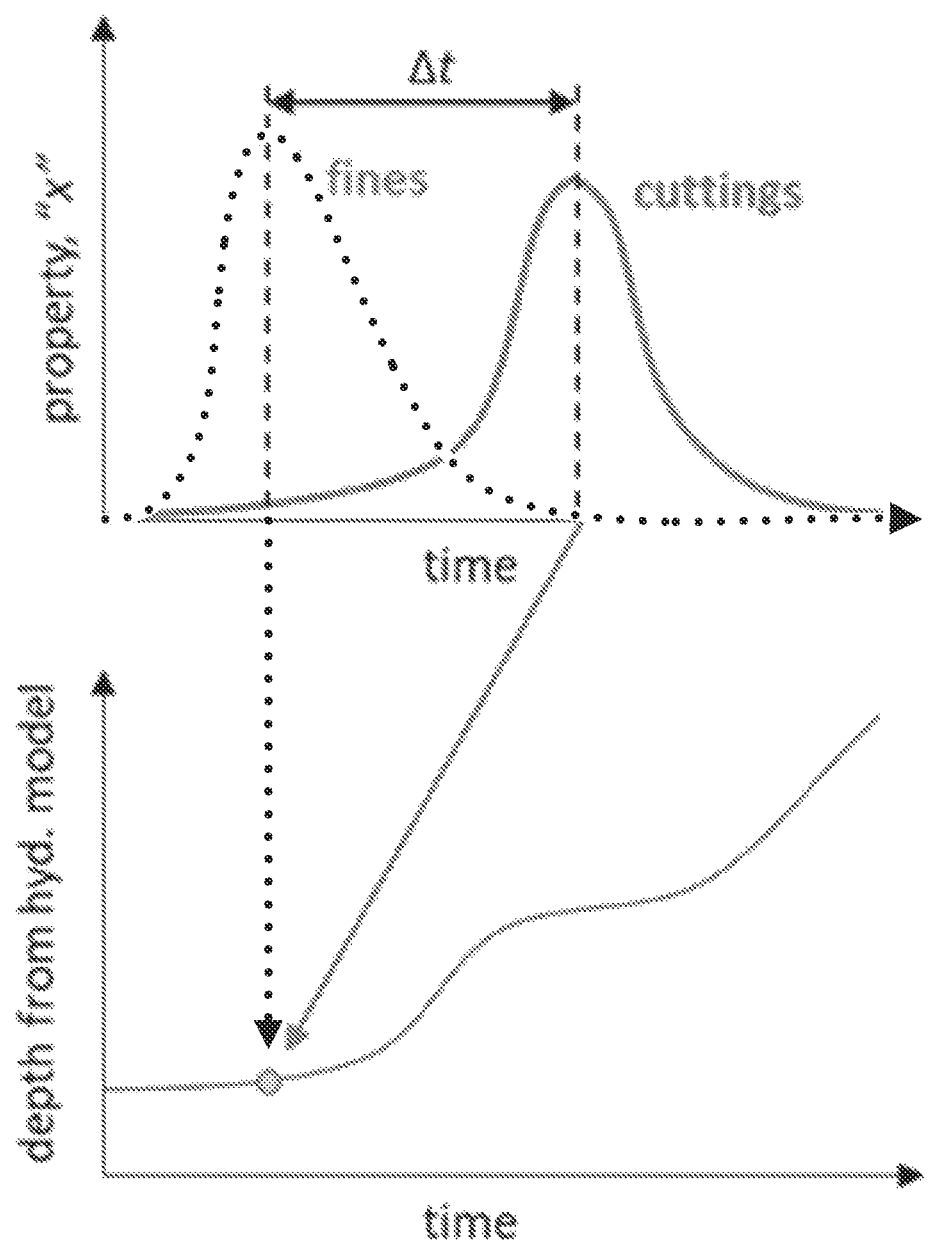
FIG. 10 is a schematic plot of depth matching of cuttings and fines separated by a transport lag using measurement logs, according to some embodiments of the present disclosure.

In some methods according to the present disclosure, the fines analysis described herein is a foundation for depth-matching of cuttings by one or more additional analysis techniques. For example, FIG. 10 illustrates an example of time-displaced correlation between at least one property of the fines and the cuttings. In some embodiments, at least one property of the fines from the drilling fluid is measured to create a log of fines values for the at least one property. At least one fines value of the log of fines values is compared to cutting values of a log of cutting values measured from the drilling fluid for the same property. The log of fines values is correlated to a hydrological model based at least partially on the flow rate of the drilling fluid, as the transport rate of the fines is approximately that of the flow rate of the drilling fluid.

Continuous or substantially continuous measurement of the drill solids transported from the wellbore by the drilling fluid allows correlation of the measured property between the fines and cuttings despite difference in transport rate (such as described in relation to FIG. 8) and/or the lag in the transport (such as described in relation to FIG. 9). When a cuttings value of the measured property of the cuttings is within a threshold value of a fines value of the measured property of the fines, the cuttings are depth matched to the fines. Since the depth of the wellbore/BHA that produced the fines is known, the cuttings can be correlated to the depth from which the matched fines were received.

In some embodiments, the threshold value is a percentage of the fines value for the measured property. For example, if the measured property is aluminum concentration, the threshold value may be a 10% variance (above or below) from the fines value for the aluminum concentration. In some embodiments, the threshold value is less than 10% variance from the fines value. In some embodiments, the threshold value is less than 5% variance from the fines value. In some embodiments, the threshold value is less than 2% variance from the fines value.

In some embodiments, the measured property includes the magnetic susceptibility. For example, the measured property can be measured using an NMR spectrometer according to the methods described herein or other methods that would be appreciated by one of ordinary skill in view of the disclosure herein. The magnetic susceptibility is measured for both the fines and the cuttings to depth match the cuttings relative to the fines. Upon depth matching of the cuttings, additional analysis may be performed on the cuttings.

In other embodiments, the measured property includes an elemental content, such as aluminum content, iron content, silicon content, carbon content, etc. In other examples, the measured property includes a particular chemical content, such as carbonates, oxides, or other representative chemical contents that are not single element measurements. The measurement techniques can include one or more of optical lithology, diffuse infrared Fourier transform spectroscopy (DRIFTS), laser-induced breakdown spectroscopy (LIBS), Raman spectroscopy, Terahertz spectroscopy, XRF, XRD, continuous wave technology (CWT) acoustics, other spectroscopy techniques, other mineral identification techniques, or combinations thereof. While NMR is described herein to provide bulk measurements with limited sample preparation, other techniques can be applicable depending on the expected mineralogy, such as the noted examples of barite clays or ferrous-rich samples which may complicate NMR measurements.

In at least one embodiment, the fines are evaluated using XRF to measure an elemental and/or chemical property of the fines. The XRF measurements can provide elemental and/or chemical properties, such as quantitative measurements of elemental composition and/or qualitative changes in elemental ratios. The elemental and/or chemical properties can be compared to downhole logs to correlate the fines values to the downhole environment based on either the quantitative measurements, the qualitative measurements, or both. For example, a qualitative shift in the elemental and/or chemical properties can indicate a transition between rock formations in the downhole environment, even absent a precise quantitative elemental composition measurement.

Cuttings can be evaluated using XRF to measure an analogous elemental and/or chemical property (e.g., quantitative or qualitative) of the cuttings. In some embodiments, a quantitative elemental and/or chemical measurement allows a direct match between composition of the fines and the cuttings. In some embodiments, a qualitative elemental and/or chemical measurement allows a boundary of a rock formation to be identified and correlated to the qualitative boundary of the fines values. In some embodiments, the fines log of the elemental and/or chemical properties can, therefore, be compared to and correlated with the cuttings logs as each are continuously or substantially continuously measured.

In some embodiments, the measured property is measured using different analysis techniques for the fines and cuttings. For example, the measured property is measured in the fines using a first analytic technique and measured in the cuttings using a second analytic technique. For example, different spectroscopy techniques may be used to measure elemental composition, while the different spectroscopy techniques collect measurements more accurately and/or faster with the fines or the cuttings. In some embodiments, the measured property is measured for the fines and cuttings using the same analysis technique.

Optical lithology can provide an array of physical properties. In some embodiments, optical lithology can allow a user (or an automated system) to measure grain size, grain aspect ratio, color, crystal structure, polarized (plane and/or cross) light transmission, and other optical mineralogical properties. In some embodiments, optical lithology can be automated through image recognition procedures in a microscope to measure statistically significant quantities of grains in the fines and/or cuttings.

In some embodiments, DRIFTS can be used to determine mineralogy with minimal cuttings cleaning. DRIFTS can be used at the drill site or other location for continuous or substantially continuous measurement of at least one property for depth-matching between fines and cuttings. Reflected infrared light provides a spectrum from a sample. By comparison to known standard spectra, it is possible to determine the mineral composition of a rock sample. Whole mud can also be analyzed by DRIFTS.

Raman spectroscopy is an alternative vibrational spectroscopy technique, which can be used as an alternative to or in addition to DRIFTS. Raman spectroscopy can also be utilized at the drill site or other location for continuous or substantially continuous measurement of at least one property for depth-matching between fines and cuttings. Similar to DRIFTS, Raman spectroscopy can also be used to study the whole mud.

Terahertz spectroscopy is another vibrational spectroscopy technique, which evaluates a different frequency range than DRIFTS or Raman spectroscopy. Terahertz spectroscopy may be used as an alternative to or in addition to DRIFTS and/or Raman spectroscopy for continuous or substantially continuous measurement of at least one property for depth-matching between fines and cuttings.

LIBS is, in contrast, a destructive sampling technique. A focused laser atomizes a small volume of sample to create a plasma. The spectrum of light emitted by the plasma is analyzed to determine the elemental composition of the sample. In some embodiments, the laser provides a first pulse to vaporize the drilling mud, and then a second pulse can atomize a portion of the rock.

XRF exposes the sample to an X-ray source, which excites at least a portion of the sample. The excited atoms of the sample then emit secondary X-rays upon relaxation. XRF records the characteristic emission of secondary X-rays from the sample to provide an elemental analysis. This method is commonly used for metal analysis, as well as earth formation analysis. Bench-top and hand-held XRF devices are available for drill site or other location sample analysis that provides continuous or substantially continuous measurement of at least one property for depth-matching between fines and cuttings.

CWT acoustics measures the sound velocity in rock samples to determine mineralogy and/or composition. It is suitable for application to small (sub-millimeter) cuttings (i.e., fines) as well as larger cuttings for continuous or substantially continuous measurement of at least one property for depth-matching between fines and cuttings. Acoustic measurements are sensitive to geomechanical properties of the formation.

Figure 11:
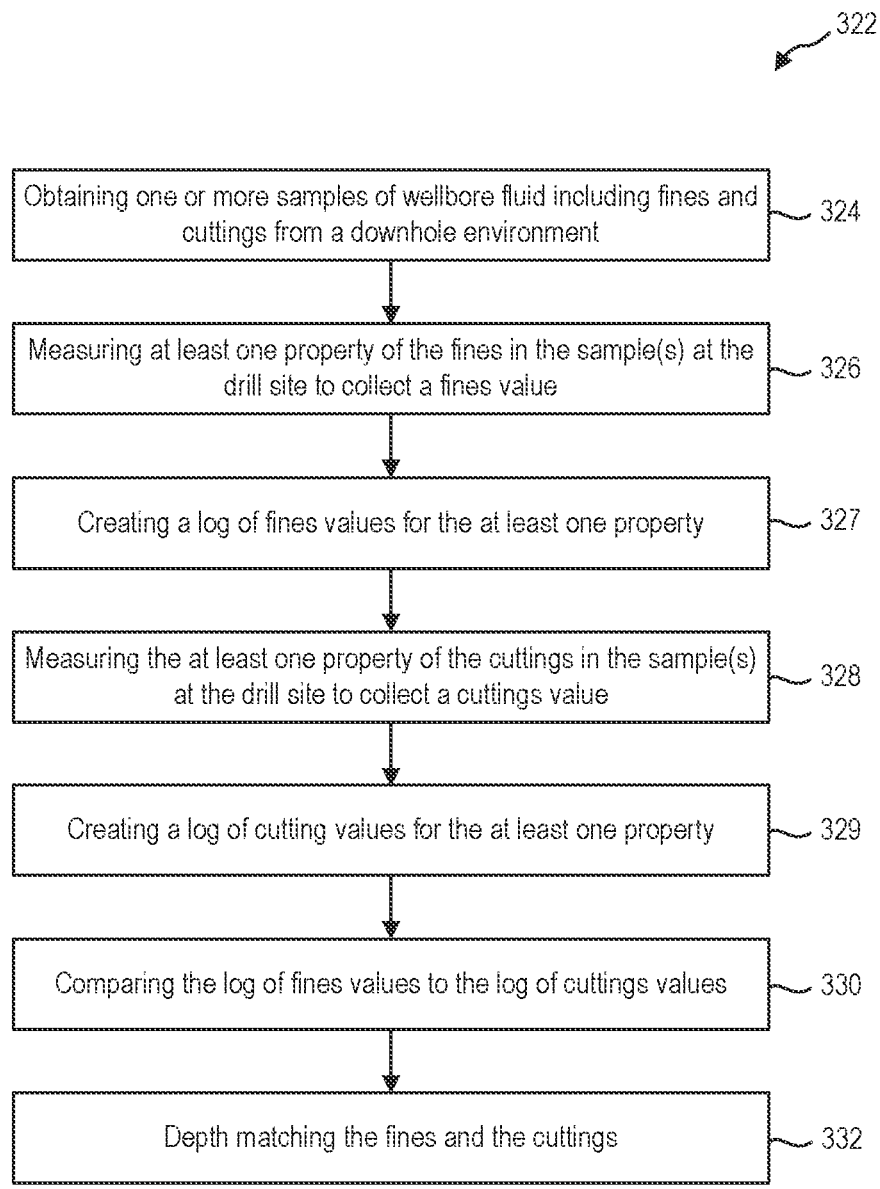
FIG. 11 is a flowchart illustrating a method of depth matching fines and cuttings, according to some embodiments of the present disclosure.

FIG. 11 is a flowchart illustrating a method 322 of depth matching cuttings and fines from a downhole environment. In some embodiments, the method 322 includes obtaining one or more samples of fluid including fines and cuttings from a downhole environment at 324. In some embodiments, the fluid is or includes a drilling fluid returning to the surface after being used in a drilling or other downhole operation. In some embodiments, obtaining the sample(s) is similar to obtaining the sample described in FIG. 2.

In some examples, the fines have an average or median diameter of less than 0.5 mm. In some examples, the fines have an average or median major axis less than 0.5 mm. In some examples, the fines have an average or median of 0.5 mm between the major axis and the minor axis. In some embodiments, the one or more samples further include cuttings. As described herein, the cuttings can include particles larger than the fines (e.g., including particles between 1 and 3 mm in size). In some examples, the cuttings have an average or median diameter between 1 and 3 mm. In some examples, the particles have an average or median major axis between 1 and 3 mm. In some examples, the particles have an average or median of between 1 and 3 mm between the major axis and the minor axis.

Obtaining the sample from the downhole environment includes, in some embodiments, collecting the sample(s) from fluid at the surface of the wellbore. In some embodiments, obtaining the sample(s) includes collecting the sample(s) after the fluid has passed over, through, or around a magnet that removes some or all of the ferrous and/or ferromagnetic material from the fluid. In some embodiments, obtaining the sample(s) includes filtering a portion of the fluid to remove particles larger than the fines. For example, the fines and cuttings may be separated at a shaker table. In some embodiments, obtaining the sample(s) includes collecting the sample(s) from the shaker table or downstream of the shaker table. In some embodiments, obtaining the sample(s) includes collecting the sample(s) after one, more than one, or each of the solid control equipment. In some embodiment, obtaining the sample(s) includes collecting the sample(s) from the suction outlet of an active tank.

The fines are suspended in the sampled fluid. In some embodiments, the fluid is an oil-based drilling fluid. In some embodiments, the fluid is a water-based drilling fluid. In some embodiments, the fines and cuttings are separated to allow independent analysis of the fines and the cuttings. In some embodiments, the one or more samples include both the fines and cuttings during analysis.

The method 322 as shown in FIG. 11 further includes measuring at least one property of the fines in the sample(s) to collect a fines value at 326 and creating a log of fines values for the at least one property at 327. The method 322 can further include measuring the same property of the cuttings in the one or more samples to collect a cuttings value at 328, and creating a log of cutting values for the property at 329. Measuring the property (or properties) of the fines and the cuttings can be performed by one or more of the analysis techniques described herein, and at any of a variety of locations. In some embodiments, the analysis technique used to analyze the fines is the same analysis technique used to analyze the cuttings. In other embodiments, the fines and cuttings are analyzed with different techniques. In some embodiments, measuring the property of the cuttings at 328 and/or the fines at 326 occurs at the drill site. In the same or other embodiments, measuring the property of the cuttings at 328 and/or of the fines at 326 occurs at a laboratory or other location away from the drill site.

The logs can include a continuous, substantially continuous, or periodic measurement of the at least one property during drilling operations and/or while fluid is flowing through the wellbore. In some embodiments, the logs include measurements taken every minute, every 5 minutes, every 10 minutes, every 15 minutes, every 30 minutes, every hour, etc. In other embodiments, the logs are performed on an ad hoc basis to provide occasional measurements at irregular intervals. Because the techniques described herein, and, in particular, magnetic susceptibility in an NMR spectrometer, are available at the drill site (for example, in an online rheometer, on-site laboratory, or control office), the analysis can be performed with little to no delay between sample collection and data collection.

In some embodiments, the method 322 further includes comparing the log of fines values to the log of cuttings values at 330. As described herein, the comparison can include matching the fines value and cuttings value, optionally within a threshold value or difference. The comparison allows the identification of when cuttings with the same value for the measured property appear in the drilling fluid as the fines from the same provenance in the wellbore. Once the fines and cuttings are depth matched at 332, in some embodiments, the transport lag or delay between the fines and cuttings can be determined and applied to some or all of the logs for the same drilling and drilling fluid parameters.

The embodiments of drilling solids analysis have been primarily described with reference to wellbore cutting operations; however, the drilling solids analysis described herein may be used in applications other than the drilling of a wellbore. In other embodiments, drilling solids analysis according to the present disclosure may be used outside a wellbore or other downhole environment used for the exploration or production of natural resources. For instance, the drilling solids analysis of the present disclosure may be used in a borehole used for placement of utility lines, for geothermal well placement, for in-situ mining, or for exploratory wells. Accordingly, the terms "wellbore," "borehole" and the like should not be interpreted to limit tools, systems, assemblies, or methods of the present disclosure to any particular industry, field, or environment.

One or more specific embodiments of the present disclosure are described herein. These described embodiments are examples of the presently disclosed techniques. Additionally, in an effort to provide a concise description of these embodiments, not all features of an actual embodiment may be described in the specification.

Additionally, it should be understood that references to "one embodiment" or "an embodiment" of the present disclosure are not intended to be interpreted as excluding the existence of additional embodiments that also incorporate the recited features. For example, any element described in relation to an embodiment herein may be combinable with any element of any other embodiment described herein, to the extent such features are not described as being mutually exclusive. Numbers, percentages, ratios, or other values stated herein are intended to include that value, and also other values that are "about", "substantially", or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

The terms "approximately," "about," and "substantially" as used herein represent an amount close to the stated amount that is within standard manufacturing or process tolerances, or which still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims. The described embodiments are therefore to be considered as illustrative and not restrictive, and the scope of the disclosure is indicated by the appended claims rather than by the foregoing description.

What is claimed is:

1. A method of measuring at least one property of a material from a wellbore, the method comprising:
    obtaining at least one sample of fluid including at least fines from a downhole environment;
    exposing the at least one sample to a magnetic field produced by a nuclear magnetic resonance (NMR) spectrometer;
    measuring a magnetic susceptibility of the fines in the at least one sample in response to the magnetic field; and
    identifying at least one mineral present in the fines based at least partially on the magnetic susceptibility.

2. The method of claim 1, wherein the at least one sample further includes cuttings from the downhole environment.

3. The method of claim 1, wherein obtaining the at least one sample includes separating at least a portion of drill solids in the fluid from the fines.

4. The method of claim 3, wherein separating the at least the portion of the drill solids includes magnetically separating ferrous material from the fluid.

5. The method of claim 1, wherein obtaining the at least one sample includes collecting the sample from or downstream of a shaker table.

6. The method of claim 1, wherein measuring the magnetic susceptibility of the fines is performed at a drill site.

7. The method of claim 1, wherein the magnetic field is up to 0.5 Tesla.

8. The method of claim 1, wherein measuring the magnetic susceptibility of the fines in the at least one sample includes measuring a magnetic susceptibility contrast between the fines and a liquid medium of the at least one sample.

9. The method of claim 1, wherein measuring the magnetic susceptibility of the fines in the at least one sample includes measuring a line broadening of an NMR spectral line.

10. A method of measuring material from a wellbore, the method comprising:
    obtaining at least one sample of fluid including at least fines from a downhole environment;
    exposing the at least one sample to a magnetic field in an NMR device;
    measuring a magnetic susceptibility contrast of the fines in the at least one sample in response to the magnetic field;
    identifying a concentration of at least one mineral present in the fines based at least partially on the magnetic susceptibility contrast;
    comparing the concentration of the at least one mineral to a mineralogy log of the downhole environment; and
    determining a provenance of the fines in the downhole environment.

11. The method of claim 10, wherein measuring the magnetic susceptibility contrast includes a free induction decay measurement using a radio frequency probe.

12. The method of claim 10, wherein determining the provenance of the fines includes measuring a flow rate of drilling fluid and comparing the flow rate to a depth of the wellbore.

13. A method of measuring material from a wellbore, the method comprising:
    obtaining at least one sample of fluid including fines and cuttings from a downhole environment;
    measuring at least one property of the fines in the at least one sample and thereby collecting a fines value;
    creating a log of fines values for the at least one property;
    measuring the at least one property of the cuttings in the at least one sample and thereby collecting a cuttings value, wherein measuring the at least one property of the fines and measuring the at least one property of the cuttings includes different analysis techniques;
    creating a log of cuttings values for the at least one property;
    comparing the log of fines values to the log of cuttings values; and
    depth matching the fines and the cuttings.

14. The method of claim 13, wherein depth matching the fines and the cuttings includes comparing the log of fines values to a drilling fluid flow rate.

15. The method of claim 13, wherein at least one of measuring the at least one property of the fines or the cuttings includes using NMR spectrometry.

16. The method of claim 13, wherein at least one of measuring the at least one property of the fines or the cuttings includes X-ray fluorescence.

17. The method of claim 13, wherein at least one of measuring the at least one property of the fines or the cuttings includes optical lithology.

18. The method of claim 13, wherein at least one of measuring the at least one property of the fines or the cuttings includes Raman spectroscopy.

* * * * *